US006511433B1

(12) United States Patent
Benjamin

(10) Patent No.: US 6,511,433 B1
(45) Date of Patent: Jan. 28, 2003

(54) ACTIVE ACOUSTIC ARRAY FOR ULTRASONIC BIOMEDICAL APPLICATIONS

(75) Inventor: Kim C. Benjamin, Portsmouth, RI (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 25 days.

(21) Appl. No.: 09/917,584

(22) Filed: Jul. 30, 2001

(51) Int. Cl.$^7$ ................................. A61B 8/00
(52) U.S. Cl. ......................... 600/463; 128/916
(58) Field of Search ................... 600/430, 443, 600/447, 449, 445, 463, 461; 178/916

(56) References Cited

U.S. PATENT DOCUMENTS

| | | | | |
|---|---|---|---|---|
| 4,545,385 A | * | 10/1985 | Pirschel | 128/915 |
| 6,117,080 A | * | 9/2000 | Schwartz | 600/443 |
| 6,122,542 A | * | 9/2000 | Lee et al. | 128/915 |

* cited by examiner

*Primary Examiner*—Francis J. Jaworski
*Assistant Examiner*—Maulin Patel
(74) *Attorney, Agent, or Firm*—Michael J. McGowan; James M. Kasischke; Michael F. Oglo

(57) ABSTRACT

The present invention relates to a device for detecting cancer in human tissue. The device comprises an acoustic array shaped to conform to and surround a portion of the human anatomy and a material for acoustically coupling the acoustic array and the human anatomy portion. The acoustic array is formed from a plurality of doubly curved segments. Each segment is formed by a piezoelectric ceramic polymer composite material with an acoustic element pattern formed on one surface via the selective deposition of a conductive material. The acoustic element pattern contains a plurality of acoustic elements which act as both transmitters and receivers. The acoustic array further includes a backing material which provides a desired mechanical damping to each segment and defines the shape of the array. The device further includes a housing which includes signal conditioning electronics to condition signals received from the acoustic array. A central processing unit is provided to create cross sectional images of the human tissue under examination. A display unit is provided to display the cross sectional images.

19 Claims, 4 Drawing Sheets

ACTIVE ACOUSTIC ARRAY FOR ULTRASONIC BIOMEDICAL APPLICATIONS

STATEMENT OF GOVERNMENT INTEREST

The invention described herein may be manufactured and used by or for the Government of the United States of America for governmental purposes without the payment of any royalties thereon or therefor.

CROSS-REFERENCE TO RELATED PATENT APPLICATIONS

Not applicable.

BACKGROUND OF THE INVENTION (1) Field of the Invention

The present invention relates to a device having an acoustic array, which device has utility in ultrasonic biomedical applications, particularly in the detection of breast cancer.

(2) Description of the Prior Art

Current breast cancer screening techniques which rely on X-rays are painful to undergo and often ineffective for detecting early stages of cancer. Conventional ultrasound systems, i.e., hand-held linear b-scan arrays, are limited by the maximum allowable levels of exposure to the ultrasound set forth by the Food and Drug Administration (FDA).

Ultrasound technology has been used in the medical field for many applications ranging from monitoring the heart condition of individuals to monitoring fetal development. There are a number of patents which illustrate various features of ultrasound equipment used in medical applications. For example, U.S. Pat. No. 5,042,492 to Dubut illustrates a probe used in ultrasound apparatus. The probe is formed with a concave attack face using a continuous acoustic transition blade. The blade is metallized and is in common contact with all the front metallizations of a series of piezoelectric elements of the probe. The rear metallizations of the elements terminate electrically and independently backwards of the probe. The probe has utility in ultrasound experiments where good focusing is desired.

U.S. Pat. No. 5,122,993 to Hikita et al. relates to a piezoelectric transducer which converts electric signals into sound waves or other mechanical vibrations or converts mechanical vibrations into electric signals and which has utility in the transmission/reception of sound waves into/from the human body. The piezoelectric transducer has plural piezoelectric transducer elements which can generate mechanical vibrations converging substantially on one point. The transducer is formed to control the convergent point by insulating piezoelectric transducer elements mechanically, arranging them concentrically and driving them independently and separately from each other.

U.S. Pat. No. 5,680,863 to Hossack et al. relates to a phased array transducer for an ultrasonic imaging system. The transducer includes a flexible support element which supports an array of piezoelectric transducer elements. Shape transducers such as strain gauges or capacitive transducers are coupled to the support element to generate a signal indicative of the instantaneously prevailing curvature of the array. A user-controlled actuator is coupled to the support element to flex the support element between at least first and second configurations wherein the support element has separate curvatures along the axis of the transducer in each of the first and second configurations.

U.S. Pat. No. 5,713,356 to Kruger relates to a photoacoustic breast scanner which uses incident electromagnetic waves to produce resultant acoustic waves. Multiple acoustic transducers are acoustically coupled to the surface of the tissue for measuring acoustic waves produced in the tissue when the tissue is exposed to a pulse of electromagnetic radiation. The multiple transducer signals are then combined to produce an image of the absorptivity of the tissue, which image may be used for medical diagnostic purposes.

U.S. Pat. No. 5,305,752 to Spivey et al. relates to an acoustic imaging device. The devices consist of a ring of acoustic transducers which encircle a medium to be imaged. The medium is sequentially insonified by each transducer with subsequent reception of the scattered waves by the remaining transducers. The device may be used for imaging human tissue in vivo and in vitro.

The current invention describes a stationary array amenable to repetitive averaging of the ultrasonic field at lower intensity for longer periods.

SUMMARY OF THE INVENTION

Accordingly, it is an object of the present invention to provide a device which may be used to screen human tissue for cancerous tissue.

It is a further object of the present invention to provide a device as above which has particular utility in the detection of breast cancer.

The foregoing objects are attained by the device of the present invention.

In accordance with the present invention, a device for detecting cancer in human tissue is provided. The device broadly comprises an acoustic array shaped to conform to and surround a portion of the human anatomy and means to acoustically couple the acoustic array to the portion of the human anatomy. The acoustic array is doubly curved having a first curvature along a first axis and a second curvature along a second axis perpendicular to said first axis.

BRIEF DESCRIPTION OF THE DRAWINGS

Other details of the doubly curved inward radiating acoustic array device of the present invention, as well as other objects and advantages attendant thereto, are set forth in the following detailed description and the accompanying drawings wherein like reference numerals depict like elements, wherein.

DESCRIPTION OF THE PREFERRED EMBODIMENT(S)

Referring now to FIGS. 1, 2, 3A–3C, and 4A–4B, the present invention relates to a device 10 having a doubly curved acoustic array 12 which surrounds a portion 14 of the human anatomy, such as a female breast. The acoustic array 12 is said to be doubly curved because it has a first curvature along a first axis and a second curvature along a second axis substantially perpendicular to the first axis. The device 10 is intended to screen for abnormal tissue using ultrasonic waves.

Figure 1:
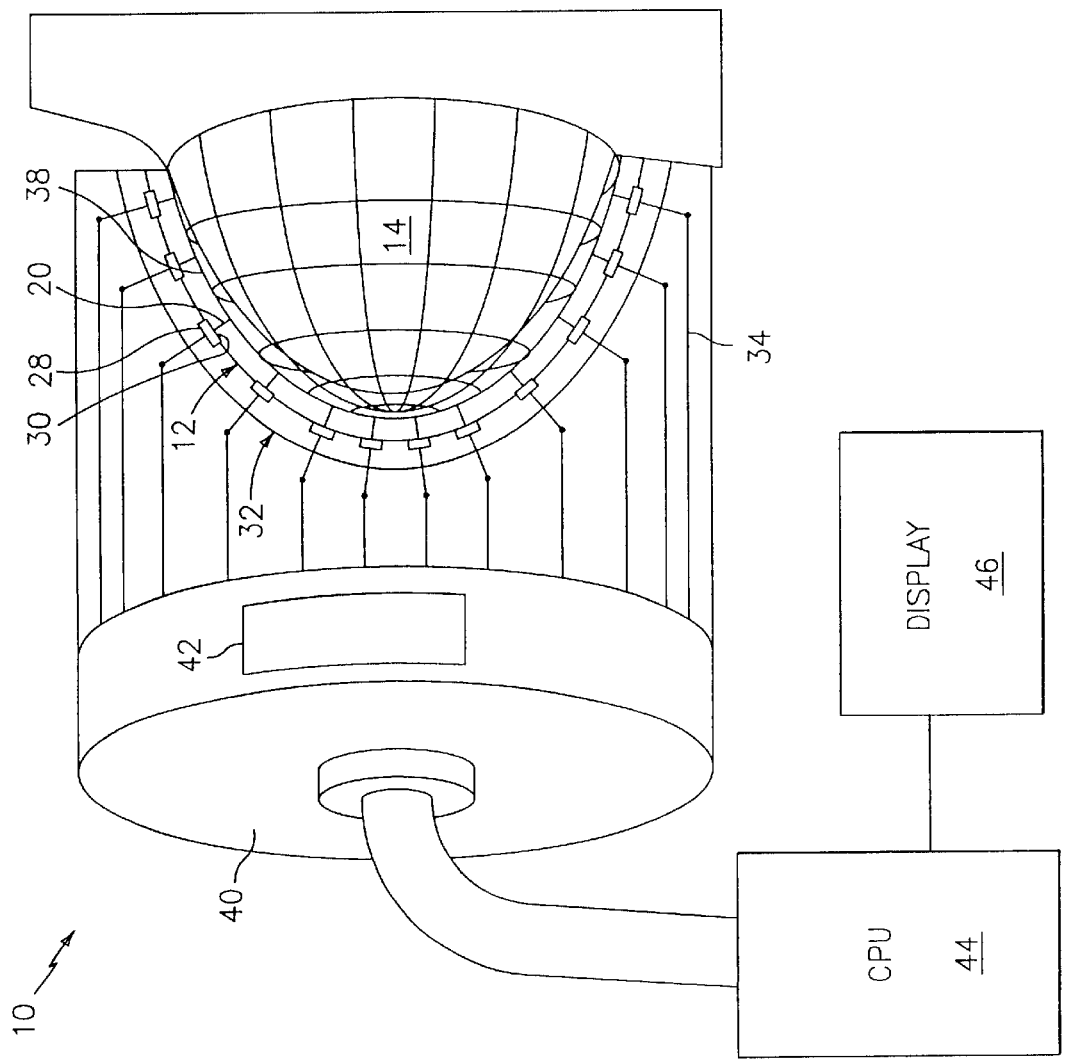
FIG. 1 is a schematic representation of a device for detecting cancer in human tissue in accordance with the present invention.
Figure 2:
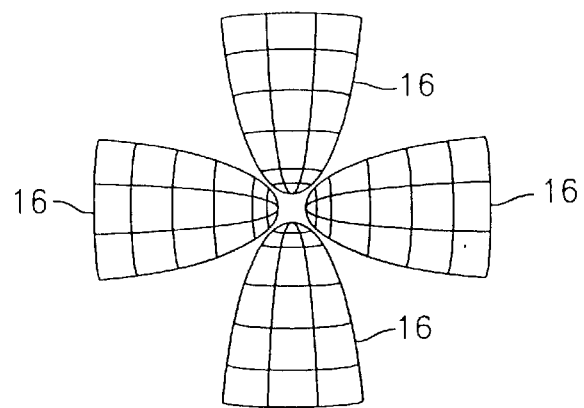
FIG. 2 is a schematic representation of the segments forming the acoustic array used in the device of FIG. 1.
Figure 3A:
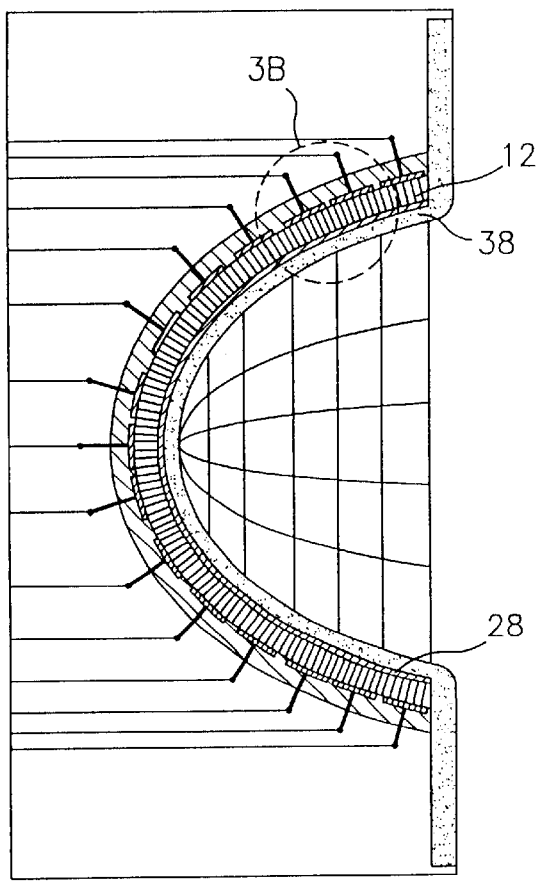
FIG. 3A is a sectional view of the acoustic array used in the device of FIG. 1 surrounding a human breast.
Figure 3B:
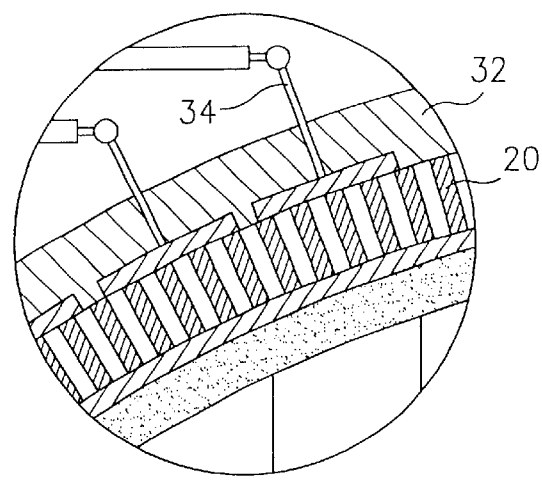
FIG. 3B is an enlarged view of a portion of the acoustic array.
Figure 3C:
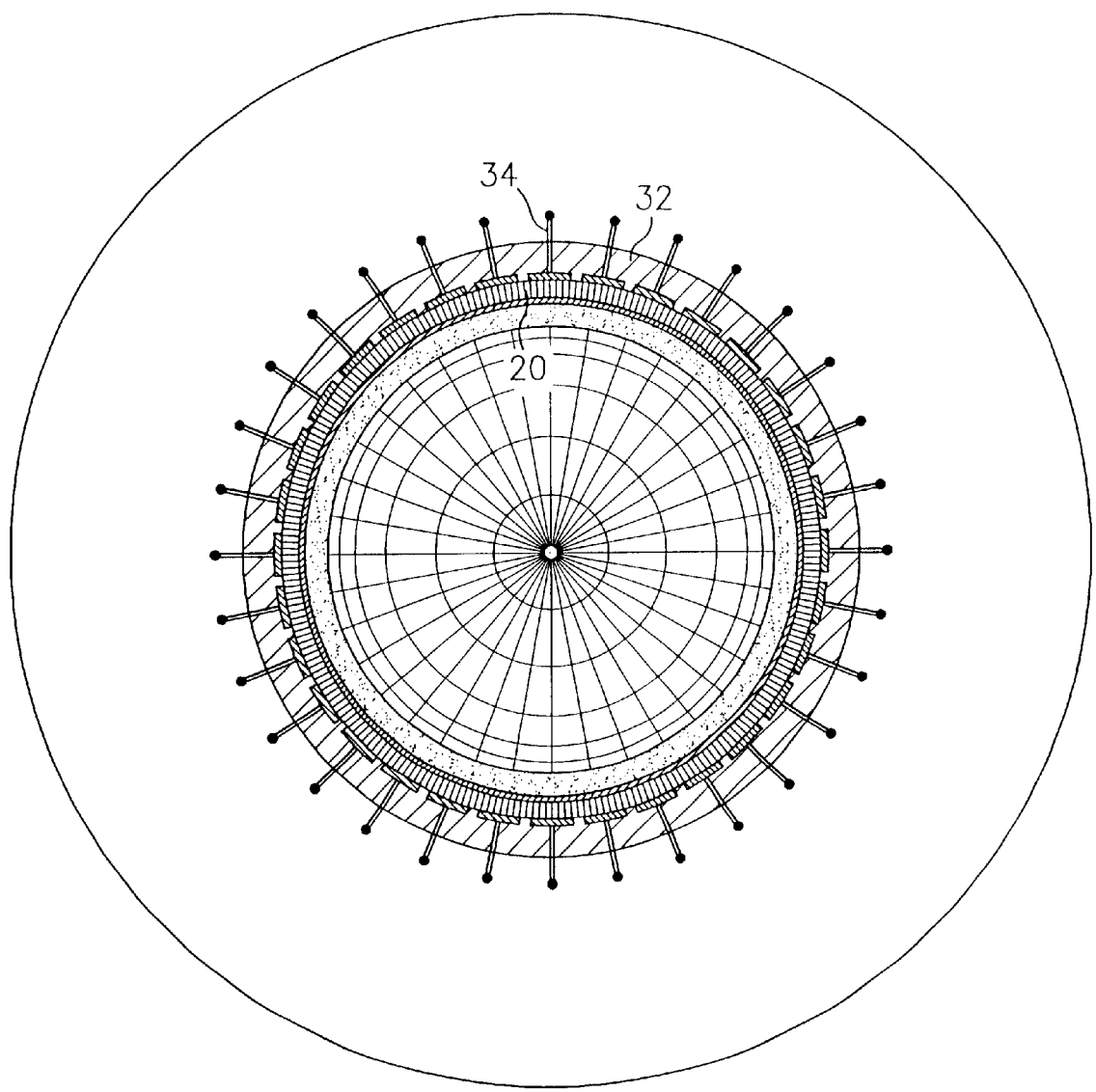
FIG. 3C is a rear view of the acoustic array of FIG. 3A.
Figure 4B:
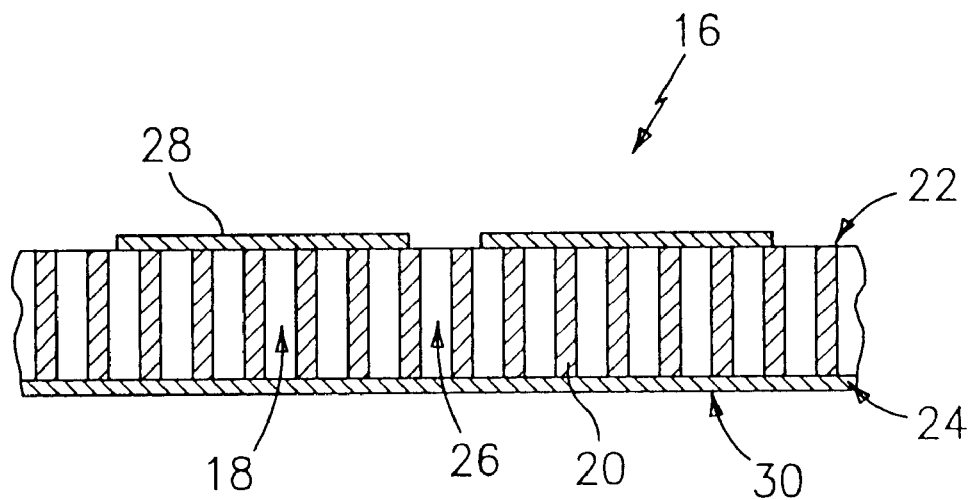
FIG. 4B is a sectional view of a flat sheet of piezoelectric material from which the acoustic array segments are formed.
Figure 4A:
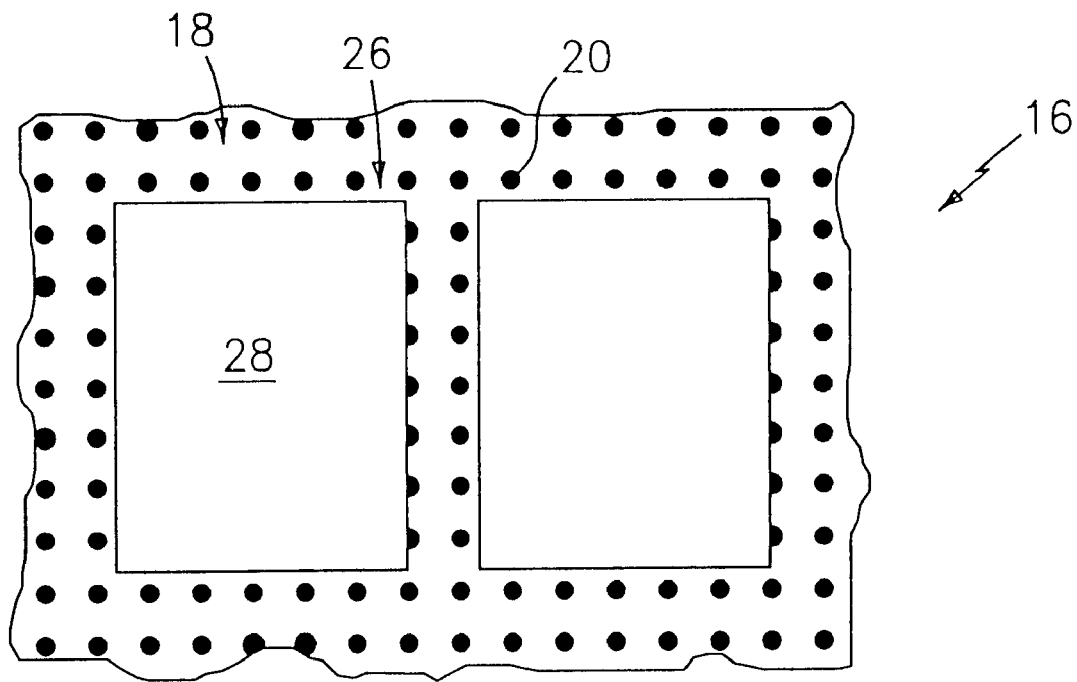
FIG. 4A is a top view of a flat sheet of piezoelectric material from which the acoustic array segments are formed.

As can be seen from FIG. 2, the acoustic array 12 is preferably formed in segments 16. Each segment 16 is formed by a flat sheet 18 of piezoelectric material as discussed below. As shown in FIG. 4, the piezoelectric material has a plurality of rods 20 formed from the piezoelectric material, such as a 1–3 piezocomposite material, extending between a first surface 22 of the sheet 18 and a second surface 24 of the sheet 18. Each of the rods 20 is surrounded by a polymeric material 26 and thus electrically and mechanically (or acoustically) insulated from adjacent rods 20. The rods 20 can have various cross sections, i.e., square, elliptical, etc.

A plurality of acoustic elements 28 are formed on the first surface 22 of the sheet by metallizing the surface 22 to form a specific pattern of acoustic elements 28 wherein the acoustic elements 28 may be randomly or regularly distributed over the array aperture. Any suitable metallizing technique known in the art, such as electroplating, can be used to form the specific pattern of acoustic elements 28. Preferably, each of the acoustic elements 28 is joined to, and thus electrically connected to, a first end of a plurality of rods 20. Each of the acoustic elements 28 functions as an acoustic transmitter and receiver.

A continuous electrode 30 is formed on the surface 24 of the sheet 18 by metallizing the surface 24 using any suitable technique known in the art, such as electroplating. Preferably, the continuous electrode 30 is formed from a copper based material. The continuous electrode 30 is formed so that it is in both physical and electrical contact with a second end of each of the rods 20 and acts as a common ground.

In a preferred embodiment of the present invention, the surface 22 comprises an outer surface of the sheet 18 and the surface 24 comprises an inner surface of the sheet 18.

As previously mentioned, the acoustic array 12 preferably has a first curvature along a first axis and a second curvature along a second axis. This is achieved by taking the flat sheet 18 forming each segment 16 and developing a desired curvature to the sheet. This may be done using any suitable technique known in the art. Preferably, the profile of each segment 16 is obtained from the mercator projection of the curved surfaced onto a flat plane. A thermoplastic, back fill material 26 surrounding the rods 20 is used to allow the segments 16 to be curved at an elevated temperature and then cooled to provide a particular parabolic geometry, such as that shown in FIGS. 1 and 3. In the present invention, a parabolic geometry is used so that the acoustic array 12 formed by the segments 16 has a shape which conforms to and surrounds a portion 14 of the human anatomy, such as a female breast.

Electrical wires or cables 34 extend through the backing material 32. Each wire or cable 34 is connected to one of the acoustic elements 28 at one end and to a voltage source 36 at the opposite end. The voltage source 36 is used to excite one of the acoustic elements 28 at a time and thus cause an ultrasonic sound wave to be generated into the portion 14 of the human anatomy. As previously mentioned, each of the acoustic elements 28 acts as both a transmitter and a receiver. Thus, when one of the acoustic elements 28 is excited, the other acoustic elements 28 act as receivers for detecting the reflected sound wave.

The acoustic array 12 is acoustically coupled to the portion 14 by a coupling material 38. The coupling material 38 must be a suitably contained lossless fluid. This fluid should be a biocompatible, non-toxic material such as silicone or water.

The device 10 further has a housing 40. The acoustic array 12 is positioned within the housing 40. The backing material 32 serves to decouple the acoustic array 12 from the housing 40 and provides acoustic impedance for a wide spatial bandwidth. The backing material 32 may comprise any suitable acoustically absorptive material known in the art. The housing also contains signal conditioning electronics 42 and the voltage source 36. The signal conditioning electronics 42 receive electric signals received by the acoustic elements 28 and are connected to the acoustic elements 28 via the wires or cables 34. The signal conditioning electronics 42 may be used to filter the signals received from the acoustic elements 28 to eliminate unwanted noise and to perform such other signal conditioning techniques as may be needed.

The device 10 further includes a central processing unit 44 and a display 46. The central processing unit 44 may comprise any suitable computer known in the art and may be programmed in any desired language. The central processing unit 44 is in communication with the signal conditioning electronics 42 and receives signals therefrom. The central processing unit 44 then converts the signals into acoustic images of the human tissue under examination of selected volume in cross section. Multiple pitch-catch views are combined to form each desired cross sectional image. This effectively halves the acoustic path length required in typical pulse-echo scenarios. In addition, the stationarity of the acoustic array 12 allows for spatial over sampling and time averaging schemes to be employed which further relax the transmit ultrasonic power levels to within current dosage maximums. The central processing unit 44 may use any suitable technique known in the art to generate 3-dimensional images. The display 46 is used to display the images generated by the central processing unit 44.

The central processing unit 44 is also preferably used to control the order in which the acoustic elements 28 are excited and to apply a broadband signal to the acoustic elements 28.

In operation, a first one of the acoustic elements 28 is excited by sending a first signal to it from the voltage source 36, such as an alternating voltage source, and placing an electric field (voltage) across the piezoelectric material forming an element within the sheet 18. The piezoelectric material in response to the electric field changes shape and gets thicker or thinner based on the instantaneous alternating voltage. This creates an initial acoustic wave having a broadband frequency content which then enters the human tissue under examination. When the initial acoustic wave encounters a change in specific acoustic impedance, such as a tumor, part of the acoustic wave is reflected and the remainder is transmitted. The reflected and transmitted waves are then detected or received by the other acoustic elements 28. The receiver elements 28 then convey the received signal to the signal conditioning electronics 42. This process is repeated over and over so that each of the acoustic elements 28 in the array 12 is used as a transmitter. In this way, a user of the device 10 can obtain an accurate picture of any tumor(s) in the human tissue under examination as well as a determination of the size, shape, and location of such tumor(s).

The device 10 and the acoustic array 12 are ideal for making tomographic scans since the acoustic elements 28 are spatially fixed with respect to each other. The inherent measurement stability and repeatability provided by the acoustic array 12 allows physicians or medical technicians to establish a pre-cancer baseline image for a given patient for future reference.

Another advantage of the present invention is that the acoustic array 12 can be sized for variations in breast size.

While the present invention has been described in the context of detecting cancer in a human breast, it should be recognized that the device can be adapted to detect cancer in other portions of the human anatomy.

It is apparent that there has been provided herein a doubly curved inward radiating acoustic array for ultrasonic medical applications which fully satisfies the objects, means, and advantages set forth hereinbefore. While the present invention has been described in the context of specific embodiments thereof, other alternatives, modifications, and variations will become apparent to those skilled in the art having read the foregoing description. Accordingly, it is intended to embrace those alternatives, modifications, and variations which fall within the broad scope of the appended claims.

What is claimed is:

1. An acoustic device comprising:
   an acoustic transducer material having a plurality of piezoelectric columns positioned in a polymeric material, said acoustic transducer material having a first surface and a second surface;
   an element pattern of individual conductive elements disposed in electrical contact with said first surface of said acoustic transducer material and contacting at least one said piezoelectric column; and
   a continuous electrode disposed on said second surface of said acoustic transducer material in contact with said piezoelectric columns, said individual conductive element, said at least one piezoelectric column and said continuous electrode comprising an acoustic element.

2. The device of claim 1 wherein said first surface is an outer surface and said continuous electrode is positionable for transmitting and receiving acoustic signals.

3. The device of claim 2 further comprising acoustic coupling means positioned on said continuous electrode.

4. The device of claim 3 wherein said acoustic coupling means comprises a biocompatible material.

5. The device of claim 3 wherein said acoustic coupling means comprises a contained lossless fluid.

6. The device of claim 1 further comprising an excitation means selectively electrically joined to each said individual conductive element for exciting the associated acoustic element.

7. The device of claim 6 wherein said excitation means comprises an alternating voltage source.

8. The device of claim 6 further comprising a signal receiving means selectively electrically joined to each said individual conductive element for receiving signals from the associated acoustic element.

9. The device of claim 1 further comprising:
   a housing surrounding said acoustic transducer material and said element pattern; and
   a backing material positioned between said housing and said first surface of said acoustic transducer material and said element pattern, said backing material decoupling said plurality of piezoelectric columns from said housing and having acoustic impedance for a wide spectral bandwidth.

10. The device of claim 9 wherein said backing material comprises an acoustically absorptive material.

11. The device of claim 9 further comprising a processing means joined electrically to each said conductive element for selectively exciting the associated acoustic element and for selectively receiving signals from the associated acoustic element.

12. The device of claim 11 further comprising signal conditioning means connected between each said individual conductive element and said processing means for filtering signals received from each said acoustic element to eliminate unwanted noise.

13. The device of claim 12 wherein said processing means further comprises:
   a controller exciting at least one acoustic element for transmission of an acoustic signal and joining at least one acoustic element for receiving said transmitted signal;
   a signal processing means joined to said signal conditioning means; and
   acoustic imaging means joined to said signal processing means.

14. The device of claim 13 further comprising a display means joined to said processor acoustic imaging means for displaying acoustic images.

15. The device of claim 1 wherein said acoustic transducer material, said continuous electrode and said element pattern have a first curvature along a first axis and a second curvature along a second axis.

16. The device of claim 15 wherein said first curvature and said second curvature are formed to substantially surround a portion of the human anatomy.

17. An acoustic imaging device comprising:
   a rigid housing having a sensor cavity;
   a backing material positioned in said housing sensor cavity for acoustic insulation;
   an array of acoustic sensors positioned in three dimensions on said backing material in said housing sensor cavity; and
   a processing means selectively electrically joined to each sensor of said array of sensors for transmitting and receiving acoustic signals from each sensor.

18. The device of claim 17 further comprising signal conditioning means connected between each said acoustic sensor and said processing means for filtering signals received from each said acoustic sensor to eliminate unwanted noise.

19. The device of claim 18 wherein said processing means further comprises:
   a controller exciting at least one acoustic sensor for transmission of an acoustic signal and joining at least one acoustic sensor for receiving said transmitted signal; and
   a signal processing means joined to said signal conditioning means.

* * * * *